(12) United States Patent
Lingenberg

(10) Patent No.: US 9,921,186 B2
(45) Date of Patent: Mar. 20, 2018

(54) METHOD AND DEVICE FOR THE NON-DESTRUCTIVE INSPECTION OF A ROTATIONALLY SYMMETRIC WORKPIECE HAVING SECTIONS WITH DIFFERENCE DIAMETERS

(71) Applicant: GE Sensing & Inspection Technologies GmbH, Hürth (DE)

(72) Inventor: Dieter Lingenberg, Hürth (DE)

(73) Assignee: General Electric Company, Schenectady, NY (US)

( * ) Notice: Subject to any disclaimer, the term of this patent is extended or adjusted under 35 U.S.C. 154(b) by 234 days.

(21) Appl. No.: 14/651,582

(22) PCT Filed: Oct. 11, 2013

(86) PCT No.: PCT/EP2013/071282
§ 371 (c)(1),
(2) Date: Jun. 11, 2015

(87) PCT Pub. No.: WO2014/090434
PCT Pub. Date: Jun. 19, 2014

(65) Prior Publication Data
US 2015/0330948 A1 Nov. 19, 2015

(30) Foreign Application Priority Data
Dec. 11, 2012 (DE) .................. 10 2012 112 121

(51) Int. Cl.
*G01N 29/00* (2006.01)
*G01N 29/22* (2006.01)
(Continued)

(52) U.S. Cl.
CPC ............. *G01N 29/00* (2013.01); *G01N 23/18* (2013.01); *G01N 29/043* (2013.01);
(Continued)

(58) Field of Classification Search
CPC ...... G01N 23/18; G01N 29/38; G01N 29/221; G01N 29/043; G01N 29/069; G01N 29/44; G01N 27/9046; G01N 2291/0289
See application file for complete search history.

(56) References Cited

U.S. PATENT DOCUMENTS 3,572,087 A * 3/1971 Parks ................... G01N 29/02
73/597
4,481,471 A 11/1984 Miller et al.
(Continued)

FOREIGN PATENT DOCUMENTS

GB 2285129 A 6/1995
WO 2008010712 A1 1/2008

OTHER PUBLICATIONS

Prashanth Kumar Chinta, U.S. Appl. No. 14/105,575, filed Jun. 11, 2015.
(Continued)

*Primary Examiner* — Ajay Ojha
(74) *Attorney, Agent, or Firm* — Barclay Damon LLP

(57) ABSTRACT

A method and a device for the non-destructive inspection of a rotationally symmetric workpiece having sections with different diameters by a non-destructive inspection technique, such as ultrasound, are provided. Within the context of the method, a test data set characterizing the material properties of the workpiece is generated by the inspection technique. An azimuth angle-dependent indicated value set is generated therefrom. Subsequently, a representation of the workpiece is generated, wherein the elements of the indicated value set are depicted in the representation in a spatially resolved manner. In particular, a graphic representation of the surface of the workpiece can be generated in which flaw signals are displayed that may have been found.

24 Claims, 4 Drawing Sheets

(51) Int. Cl.
*G01N 29/38* (2006.01)
*G01N 23/18* (2018.01)
*G01N 29/04* (2006.01)
*G01N 29/06* (2006.01)
*G01N 29/44* (2006.01)
*G01N 27/90* (2006.01)

(52) U.S. Cl.
CPC ......... *G01N 29/069* (2013.01); *G01N 29/221* (2013.01); *G01N 29/38* (2013.01); *G01N 29/44* (2013.01); *G01N 27/9046* (2013.01); *G01N 2291/0289* (2013.01)

(56) References Cited

U.S. PATENT DOCUMENTS

| | | |
|---|---|---|
| 5,311,128 A | 5/1994 | Lareau et al. |
| 2003/0089171 A1 | 5/2003 | Kenefick et al. |
| 2004/0148730 A1 | 8/2004 | Knight et al. |
| 2008/0006091 A1 | 1/2008 | McKeon |
| 2008/0041160 A1 | 2/2008 | Wright |
| 2009/0320599 A1 | 12/2009 | Burat et al. |
| 2010/0031751 A1 | 2/2010 | Perkins et al. |
| 2010/0170344 A1* | 7/2010 | Lesage ............... G01N 29/0609 73/632 |
| 2011/0083512 A1 | 4/2011 | Imbert et al. |
| 2012/0060611 A1 | 3/2012 | Thommen-Stamenkov et al. |
| 2012/0191377 A1* | 7/2012 | Engl .................... G01N 29/069 702/39 |

OTHER PUBLICATIONS

International Search Report and Written Opinion issued in connection with related PCT Application No. PCT/EP2013/071287 dated Jan. 10, 2014.

International Search Report and Written Opinion dated Mar. 5, 2014 which was issued in connection with PCT Patent Application No. PCT/EP13/071282 which was filed on Oct. 11, 2013.

German Search Report issued in connection with related Application No. 102012112121.4 dated Sep. 2, 2013.

Erhard et al., "Ultrasonic Phased Array System for Railroad Axle Examination", AIAA(90-2421) Experimental Turbofan Using Liquid Hydrogen and Liquid Natural Gas as Fuel, In: NDT.net, vol. 8, No. 3, pp. 1-6, Mar. 2003.

\* cited by examiner

METHOD AND DEVICE FOR THE NON-DESTRUCTIVE INSPECTION OF A ROTATIONALLY SYMMETRIC WORKPIECE HAVING SECTIONS WITH DIFFERENCE DIAMETERS

BACKGROUND

The subject matter of the present invention is a method and a device for the non-destructive inspection of a rotationally symmetric workpiece having sections with different diameters by means of a non-destructive inspection technique, such as ultrasound, eddy currents or X-rays. An ultrasonic inspection in accordance with the pulse echo method is used with particular preference as the inspection technique. In a particularly development, the method and the device are suited, in particular, for the inspection of a workpiece with an anisotropic sound velocity. For example, an anisotropic sound velocity is frequently observed, for example, in forged solid shafts which can be used, for instance, in rail vehicles.

The non-destructive inspection of rotationally symmetric workpieces having sections with different diameters by means of non-destructive inspection techniques often suffers from the problem of the geometrical structure of the workpiece causing geometry-related signals of the inspection technique used. These signals are correlated with the geometry of the workpiece, which is already known as such, and therefore frequently do not contain any further information. Furthermore, these so-called "geometry echoes" in many cases have a very high amplitude. There is therefore the possibility of the intensive geometry echoes obscuring less intensive underlying signals that could be correlated with, for example, flaws to be detected in the workpiece. Due to the limited dynamics of the signal processing used within the context of the inspection technique, there is therefore a danger of geometric echoes "masking" relevant signals, e.g. flaw signals.

This issue is of particular relevance, for example, in the inspection of wheel sets of rail vehicles by means of ultrasound. Wheel sets of rail vehicles generally include one pair of wheels mounted on a rigid solid or hollow shaft. The shafts used in this case often have external diameters changing from section to section, for example defined regions for the accommodation of functional components, such as the wheels, anti-friction bearings or brake disks. It is obvious that the shafts of wheel sets of rail vehicles constitute safety-relevant components that are subject to natural wear over the long life span of rail vehicles. For this reason, their freedom from flaws has to be determined by means of non-destructive inspection methods not only during the production of wheel sets for rail vehicle. Rather, a regular inspection with regard to freedom from flaws of all components, in this case particularly the wheels as well as the shaft used, is required also over the entire life span of a wheel set. In practice, the most frequent wear phenomenon observed in shafts of wheel sets of rail vehicles is the occurrence of incipient cracks, i.e. crack-like fatigue failures that start at the surface of the respective shaft. Every rail vehicle operator therefore has to provide suitable inspection methods and devices in order to check the wheel sets of rail vehicles with regard to their freedom from flaws regularly.

Until this day, the inspection by means of ultrasound of rotationally symmetric workpieces having diameters that change from section to section, in particular of solid shafts of rail vehicles, constitutes a particularly challenging inspection task. This is based, in particular, on the fact that intensive geometry echoes, which can be superposed over the signals of the flaws to be detected, are observed in the ultrasonic inspection of rotationally symmetric workpieces having diameters that change from section to section.

Moreover, the inspection of a wheel set of a rail vehicle often entails a downtime of the rail vehicle, which is directly connected to high downtime costs due to the rail vehicle being out of service. In order to minimize them, it would be desirable to be able to inspect a fully assembled wheel set, i.e. a wheel set with assembled bearings and/or brake disks. If they are mounted, then an insonification from the shaft or from the end face (e.g. by means of a conical probe) is not possible with the ultrasound-based inspection methods known from the prior art.

Finally, the generation of an easily interpreted representation of the results of, for example, an ultrasound inspection obtained on a rotationally symmetric workpiece constitutes a problem which, as far as the applicant is aware, has so far been solved only to an insufficient extent.

SUMMARY OF INVENTION

It is therefore the object of the present invention to propose a method and a device for the non-destructive inspection of a rotationally symmetric workpiece having sections with different diameters, which is based on a non-destructive inspection technique, such as ultrasound, eddy currents or X-rays. In this case, the method is supposed to be suitable for mitigating the issue of the masking geometry echoes from the workpiece with a diameter that changes from section to section.

This object is accomplished by a method and a device described below. The dependent claims can be freely combined with each other in any way within the context of what is technically feasible. However, such a combination is not an absolute requirement.

A method according to an embodiment of the invention serves for the non-destructive inspection of a rotationally symmetric workpiece having sections with different diameters. It is based on a non-destructive inspection technique, such as ultrasound, eddy currents or X-rays, with the inspection by means of ultrasound in accordance with the pulse echo method being applied in an embodiment. The method comprises the following process steps:

a. generating by means of the inspection technique a test data set characterizing the material properties of the workpiece, with the elements of the test data set being respectively assigned to a defined test volume Vi in the workpiece, whose position in the workpiece is defined by an azimuth angle $Beta_i$, a radial distance Ri from the axis of symmetry S of the workpiece, and an X position Xi relative to the axis of symmetry S of the workpiece, the test data set including a partial set T of several elements assigned to a plurality of test volumes Vi having a common X position Xi and a common radial distance Ri but different azimuth angles $Beta_i$, b. forming an azimuth angle-dependent indicated value set Ai, wherein this step includes the differentiation of the partial set T with respect to the azimuth angle Beta, and c. generating a representation (50) of the workpiece (1), wherein the elements of the indicated value set Ai are depicted in the representation (50) in a spatially resolved manner.

In this case, the elements of the test data set can be, for example, ultrasonic echo signals originating from the test volume Vi. In particular, the elements of the test data set can include the maximum echo amplitude from the respective test volumes Vi. Particularly, in an embodiment, the elements of the test data set respectively include the coordinates (Xi, Ri, $\text{Beta}_i$) of the respective test volume Vi and the associated maximum echo amplitude. Of course, other coordinate systems can also be used instead of the cylindrical coordinates used here.

By differentiating (or finding a derivative of) the partial set T with respect to the azimuth angle Beta, signals are being generated which accompany the change of the test data during a change of the azimuth angle Beta, which can be obtained, for example, by means of a rotation of the workpiece about its axis of symmetry S by an angle of rotation Delta. Test data of a partial set T that are correlated with rotationally symmetric geometric structures and are thus to be assigned to test volumes Vi with the same coordinates Ri and Xi are identical within the limits of measuring accuracy. Such structures always generate the same echo signal irrespective of the angle of rotation Delta, for example in the case of an ultrasound inspection by means of an angle test probe placed on the workpiece surface. Within the limits of measuring accuracy as well as the artifacts that typically occur during numerical differentiation of a series of discrete values, the result of the differentiation with respect to the azimuth angle (or with respect to the rotation angle Delta which is equivalent), irrespective of the azimuth angle, is therefore the value zero, unless there is a local inhomogeneity that is dependent upon the angle of rotation. There, the superposed additional echo signal ("flaw echo") associated therewith, which as a rule is limited to a few discrete rotation angle values, causes the occurrence of at least two signals in the derivative formed by differentiation. Thus, the rising signal edge generates a "spike" (a sharp local amplitude maximum) with a positive maximum. In contrast, the falling signal edge generates a negative spike. The derivative has a zero-crossing point between the edges of the flaw echo. As a rule, the local slope values formed by differentiation are close to zero between the spikes.

An embodiment of the invention is now based upon carrying out a signal processing based on the results of the differentiation, in order to generate a graphic representation of the result of the inspection method.

For this purpose, in a first embodiment, a threshold analysis is carried out in step b. for the local slope values that result during the differentiation of the partial set T with respect to the azimuth angle Beta. Those test volumes Vi are identified in which the local slope values formed by differentiation exceed a preset (positive or negative) threshold. Thus, such test volumes are identified in which spikes are located that exceed a positive or negative minimum height. During the formation of the indicated value set A1, the maximum echo signal amplitudes detected in these test volumes are assigned to these test volumes Vi. In the simplest case, the elements of the indicated value set Ai consist of the coordinates (Xi, Ri, $\text{Beta}_i$) of the respective test volume Vi and the assigned maximum echo amplitude. If a value formed by differentiation for a test volume Vi drops below a preset threshold, the value zero is assigned to this test volume Vi. Thus, a value that is different from zero is assigned only to those test volumes Vi in which the edges of the flaw echo are located. In that case, only the edges of the flaw echo are marked in the graphic representation of the indicated values, i.e. a sharpening of the edges occurs.

In an alternative embodiment, the elements of the indicated value set Ai also consist of the coordinates (Xi, Ri, $\text{Beta}_i$) of the respective test volume Vi and the assigned maximum echo amplitude. However, all echo amplitudes that are not assigned to a test volume Vi are set to zero, in which the value formed by differentiation for the test volume Vi exceeds the preset threshold, or which lies between a test volume Vj in which the preset positive threshold is exceeded and a test volume Vk in which the preset negative threshold is exceeded.

The latter test volumes Vi can then be assigned to precisely one flaw echo.

In both embodiments of the method, the indicated value set Ai is a subset of the test data set, in particular, it is furthermore a subset of the partial set T.

Reference is made to the fact that the method according to an embodiment of the invention can be applied in those cases where test data from a workpiece are provided which are dependent at least on spatial coordinates (in this case: insonification angle Theta, azimuth angle Beta). By forming a derivative in one direction in space and the above-described threshold method, test data can be suppressed in a very simple manner in a representation of the workpiece that do not change, or change only very slowly, during a scan in this direction in space (in this case azimuth angle Beta). Thus, the method according to an embodiment of the invention and its implementation in a device according to an embodiment of the invention is not limited to the inspection of rotationally symmetric workpieces. Rather, the method and device can be used in those cases where the workpiece to be tested has extensive geometric structures that lead to a reading with the test method used. Such a structure can be a straight step or otherwise plane surface, for example.

In another development of the method according to an embodiment of the invention, the test data are obtained by insonifying ultrasonic test pulses into the workpiece at different coupling locations Ei at different defined insonification angles $\text{Theta}_i$ and subsequent recording of the ultrasonic echo signals resulting from one insonified ultrasonic test pulse, respectively, from the workpiece at the coupling location Ei at the insonification angle Theta. In this case, the coupling locations Ei can, in particular, be located on the lateral surface of the rotationally symmetric workpiece. The generation and coupling of the ultrasonic test pulses can then be carried out, for example, by means of an obliquely insonifying ultrasonic test probe comprising an ultrasonic transducer for generating the ultrasonic test pulses.

In another development of the method according to an embodiment of the invention based on the pulse echo method, a travel time interval I is selected for each ultrasonic test pulse depending on the sound path W of the ultrasonic test pulse in the workpiece, the selected travel time interval I corresponding to a preselected (e.g. a near-surface) region ROI ("region of interest") of the workpiece. Said will of interes will be explained later in more detail. Subsequently, an echo value G is generated by analyzing the ultrasonic echo signal in the selected travel time interval I. If these method steps are repeated for a plurality of rotation angles Delta of the workpiece about its axis of symmetry S, then the resulting echo values G form the test data set.

Generally, the sound path W of the ultrasonic test pulse in the workpiece is dependent on the workpiece geometry, the coupling location E, the insonification angle Theta, the insonification direction and on the acoustic properties both of the workpiece as well as of the ultrasonic test probe used for the generation of the ultrasonic test pulse. For example, the insonification direction can be defined via the inclination angle Phi of the sound propagation direction with respect to the plane defined by the axis of symmetry S and the coupling location E. In some embodiments of the method, the inclination angle Phi is zero, i.e. the sound path W and the axis of symmetry S of the workpiece span a common plane P.

The method according to an embodiment of the invention provides an inspection method which permits displaying the result of a non-destructive inspection of a rotationally symmetric workpiece with a diameter that changes from section to section in a manner that is particularly intelligible to an examiner. In this case, the representation of the workpiece surface generated according to an embodiment of the invention is two-dimensional, e.g. in the form of a C image, or it is spatial, with the spatial, i.e. three-dimensional representation being used in an embodiment. It is obvious to a person skilled in the art that the generation of a graphic representation of the workpiece described herein comprises both the generation of a data set representing a representation of the workpiece, for example in the sense of a CAD model, as well as the actual depiction of a graphic representation of the workpiece on a suitable depicting unit, e.g. on a suitable display, which can be connected, for example, to a subsequently described device according to an embodiment of the invention.

In an embodiment of the method, a point w on the surface of the representation of the workpiece is assigned to the sound path W of an ultrasonic test pulse in the workpiece. In the graphic representation of the workpiece, the indicated value of the ultrasonic test pulse assigned to such a point w is presented in a suitable manner, e.g. by a local color or brightness coding. This is described in more detail below by way of example within the context of the exemplary embodiment.

In another development of the method according to an embodiment of the invention, the ultrasonic echo signal is subjected, at least in the selected travel time interval I, to a travel time-dependent or/and insonification angle-dependent amplification. In this way, sound-attenuating effects, for example due to the geometric expansion of the sound field along the propagation direction, its attenuation in the workpiece, for example due to scattering on anisotropies, as well as a possible angular dependence of the reflection of the ultrasonic test pulse on an internal boundary surface of the workpiece, can be compensated. Consequently, flaws of the same size and orientation generate echo signals of approximately the same size, irrespective of their position in the workpiece, which in turn improves even further the interpretability of the result of the test method.

It is obvious to the person skilled in the art that the recorded ultrasonic echo signal can be subjected to a suitable signal conditioning process, e.g. for improving the signal-to-noise ratio, particularly after a digitization process. For this purpose, a variety of methods are known in prior art.

The signal-to-noise ratio can also be significantly improved if the method steps a to d. are executed several times for a fixed coupling location E and a fixed insonification angle Theta and if a mean value <G> of the generated echo values G is formed. In step e., this mean value <G> is then shown in the representation in a spatially resolved way.

In a development of the method according to an embodiment of the invention, a plurality of successive ultrasonic pulses is insonified into the workpiece at different insonification angles Theta. It is possible to vary the insonification angle Theta from pulse to pulse; however, it is also possible to vary, only after a finite series of pulses at the same insonification angle, the insonification angle for a subsequent pulse series. Thus, a mean value formation of the flaw signals to be evaluated, over a plurality of echo signals resulting from a plurality of ultrasonic test pulses coupled in at the same insonification angle Theta, improves the signal-to-noise ratio. In the process, the method according to an embodiment of the invention is carried out for each ultrasonic test pulse insonified into the workpiece. In another embodiment of the method, the position of the coupling location E on the workpiece surface relative to its axis of symmetry S is kept substantially constant in the process. "Kept substantially constant" in this context means, in particular, that the position X of an ultrasonic test probe comprising an ultrasonic transducer for generating the ultrasonic test pulses is kept constant relative to the axis of symmetry S of the workpiece. In the case of the ultrasonic test probes for oblique insonification with a variable insonification angle commonly used in practice, in which the ultrasonic transducer is disposed, for example, on a wedge-shaped leading body, the actual coupling location changes slightly if the insonification angle is changed. In a first approach this effect is to be allowed to be neglected in this case. However in a more elaborated approach this effect can be taken into account upon generation of a graphical representation of the test result.

So-called "phased array" ultrasonic test probes, which are known in the prior art and whose application in the context of the present invention will be discussed in more detail, permit an electronic tuning of the insonification angle Theta over a broad angle range. Particularly in connection with the embodiments of the method according to the invention, in which the insonification angle Theta is varied between different ultrasonic test pulses of a test pulse series, the use of such "phased array" test probes with an electronically tunable insonification angle Theta has proven to be particularly advantageous. Particular advantages are obtained if, furthermore, test probes in accordance with the teaching of the family of PCT/EP2010/0566154 are being used, with this teaching being added to the disclosure of the present application by this reference. The use of such test probes allows taking into account the curvature of the coupling surface in the axial and radial directions, which is advantageous in particular in the case of shafts of wheel sets whose shaft geometries can in part also be curved completely in the longitudinal direction, so that—at least with components such as wheels, bearings or brake disks mounted on the shaft—there is no purely cylindrical region with a constant diameter for ultrasonic coupling.

In an embodiment, the insonification of the one or more ultrasonic test pulses into the workpiece is carried out in such a way that the sound path W of the ultrasonic test pulse(s) in the workpiece and the axis of symmetry S of the rotationally symmetric workpiece span a common plane, i.e. that the sound path W of the ultrasonic test pulse(s) intersects the axis of symmetry S of the rotationally symmetric workpiece. This common plane is hereinafter also referred to as insonification plane P. This insonification geometry is characterized by the insonification direction Phi=0°.

In another development of the method according to an embodiment of the invention, the relative position of the test probe position X and the workpiece is not altered while a first part of the process of the inspection method is carried out, in which the insonification angle Theta is changed continuously. This means that the above-mentioned condition is satisfied in this first part of the process for all ultrasonic test pulses coupled into the workpiece.

In an embodiment of the method, while maintaining the position of the ultrasonic test probe relative to the axis of symmetry S of the workpiece, a series of ultrasonic test pulses is insonified into the workpiece, while the insonification angle Theta and the rotation angle Delta is varied at the same time. In this case, having gone through a predetermined interval for the insonification angle Theta, for example, a gradual relative rotary movement of the ultrasonic test probe and the workpiece is carried out about the axis of symmetry S of the workpiece. Thus, an electronic tuning of the insonification angle Theta is possible over an angle range of at least 30° to 60°, and, in an embodiment, of at least 20° to 75°. Subsequently, a relative rotary movement of the test probe and the workpiece about the axis of symmetry S of the workpiece by, for example, maximally 5°, particularly maximally 1°, and more particularly maximally 0.5°, is carried out. For this new relative position of the test probe and the workpiece, a series of ultrasonic test pulses is then insonified into the workpiece at a varying insonification angle Theta. Then, another relative rotation of the test probe and the workpiece takes place, etc. On the whole, the relative rotation angle Delta of the test probe and the workpiece about the axis of symmetry S of the workpiece over a complete test cycle is to be at least 360°, in an embodiment, it is 360° or an integral multiple of 360°.

In an alternative development of the method according to an embodiment of the invention, the insonification angle Theta and the relative rotation angle Delta of the workpiece and the ultrasonic test probe about the axis of symmetry S of the workpiece are varied simultaneously, with the rotating speed of, for example, the workpiece about its own axis of symmetry S being selected to be so low that the result is still a sufficient geometric overlap of the ultrasonic test pulses in the ROI in the workpiece.

In another development of the method according to an embodiment of the invention, two groups of ultrasonic test pulses are insonified into the workpiece. In this case, the first group of ultrasonic test pulses has a travel direction which has one component in the positive direction of the axis of symmetry S of the workpiece. In contrast, the second group of ultrasonic test pulses has a travel direction which has one component in the negative direction of the axis of symmetry S of the workpiece. In an embodiment, the first and the second groups of ultrasonic test pulses are coupled into the workpiece at substantially the same location. For this purpose, it is possible, in particular, to integrate two ultrasonic transducers into a single test probe that transmit the first and second groups of ultrasonic test pulses. By means of this development of the method according to an embodiment of the invention it is possible to virtually double the tunable angle range, and thus the sector of the workpiece to be acquired from a test probe position X (relative to the axis of symmetry S of the workpiece), which makes it possible to carry out the method with an efficiency that is increased even more.

In an embodiment, the inspection method is repeatedly carried out for different test probe positions X on the workpiece surface. This third part of the process serves for acquiring as large a (near-surface) volume of the workpiece as possible. As a rule, carrying out the method at a few discrete test probe positions X is sufficient for acquiring the entire (e.g. near-surface) volume of the workpiece to be analyzed, even in the case of ragged workpiece geometries.

If the parts of the process "rotation of the workpiece about the axis of symmetry S, variation of the insonification angle Theta and variation of the test probe position X" are run through for a workpiece, then, for most workpiece geometries, the entire volume of the workpiece to be analyzed can be transsonified with the ultrasonic test pulses and thus inspected. The representation of the workpiece surface generated therefrom according to an embodiment of the invention thus contains complete information on the result of the ultrasound inspection of the entire near-surface volume of the workpiece. Particularly informative is the graphic representation described herein of the result of the ultrasonic inspection method according to an embodiment of the invention, because a complete relative rotation of the test probe and the workpiece by 360° or an integral multiple thereof about the axis of symmetry of the workpiece has taken place during the inspection of the workpiece. Because the method is furthermore carried out starting from different test probe positions X, the entire volume of the (e.g. near-surface) region of the workpiece to be analyzed is transsonified and subsequently graphically represented—provided the rotationally symmetric workpiece has a suitable geometry.

A development of the method according to an embodiment of the invention permits the reduction of the process duration by effectively reducing the amount of data to be analyzed. This is possible by limiting the evaluation of the recorded ultrasonic echo signals, which correspond to, in part, very long travel distances of the test pulse in the workpiece that occur primarily at large insonification angles Theta, to those echo signals that result from a preselected (e.g. near-surface) region of the workpiece to be inspected. Within the context of the present invention, this preselected region is also referred to as "region of interest" (ROI). As a rule, the ROI to be used during the execution of the method is determined by the examiner with knowledge of the material properties as well as of the geometry of the workpiece. In the case of solid shafts of wheel sets of rail vehicles, the ROI is selected to be adjacent to that internal workpiece surface at which a first reflection of the ultrasonic test pulse in the workpiece occurs.

Such an ROI can be limited, for example, to the sector of the workpiece that extends radially inwardly, from the workpiece surface, by a few to a few tens of millimeters, for example by 30 to 60 millimeters, and, in an embodiment, by 40 millimeters.

Also, the ROI can be defined differently from section to section along the axis of symmetry of the workpiece, e.g. in regions with a changing shaft diameter, it can have a larger extent than in regions with a constant diameter.

Thus, ROI can also be deliberately selected to be larger in some sections, e.g. in order to depict displays from a wheel, bearing or brake seat possibly formed on the solid shaft.

Because of the existing uncertainty with regard to the sound velocity in a forged workpiece, it is advantageous to limit the ROI not only up to the incidence of the ultrasonic test pulse on the internal workpiece surface, but a certain travel time beyond, i.e. an internal total reflection on the workpiece surface may possibly occur in the ROI. However, the ultrasound testing pulse at least reaches the internal workpiece surface with a very good degree of certainty.

The travel time interval to be selected that corresponds to the ROI relates to the response time between the ultrasonic test pulse being coupled into the workpiece and the arrival of ultrasonic echo signals. The workpiece geometry is presumed to be known, as are the acoustic properties of the workpiece. Moreover, the coupling location E of the ultrasonic pulse, the insonification angle Theta and the insonification direction are known. As was already mentioned, the insonification direction can be defined, for example, via the inclination angle Phi of the sound propagation direction with respect to the plane defined by the axis of symmetry S and the coupling location E. In embodiments of the method, the inclination angle Phi is zero, i.e. the sound path W and the axis of symmetry S of the workpiece span a common plane P. The coupling location E is directly linked to the test probe position X on the workpiece surface and the insonification angle Theta. The sound path W of the ultrasonic test pulse in the workpiece can be determined from this, which, when a workpiece geometry and workpiece properties are given, is generally a function of the test probe position X, of the insonification angle Theta and of the inclination angle Phi. In particular, the travel time tROI_EIN can be determined after which the ultrasonic test pulse enters the ROI previously determined by the examiner. Furthermore, a travel time tROI_AUS can be determined after which the first reflection of the ultrasonic test pulse on an internal workpiece surface has occurred. For a given insonification angle Theta, the ROI can be defined via this travel time interval I, i.e. every echo signal recorded after a response time tAntwort with 2tROI_EIN≤tAntwort≤2tROI_AUS results from an ultrasound reflector (e.g. a local anisotropy in the material structure of the workpiece, the local workpiece geometry, a flaw) in the ROI. It is obvious that the travel time interval I is, as a rule, dependent on the given insonification angle Theta.

In a development, the ROI is defined via the travel time interval I selected (and thus to be analyzed) for a given insonification angle Theta. The basis is the sound velocity for the ultrasonic test pulse in the workpiece, which can be specified only with a certain uncertainty. The start of the travel time interval I is defined by the time 2tROI_EIN at which the ultrasonic test pulse hits the internal surface for the first time at the earliest, i.e. the highest possible sound velocity is used as a basis. The end of the travel time interval I is defined by the time 2tROI_AUS at which the ultrasonic test pulse hits the internal surface for the first time at the latest, i.e. the lowest possible sound velocity is used as a basis. It is thus ensured that the ultrasonic test pulse hits the internal workpiece surface in the selected travel time interval with certainty, i.e. the internal surface lies within the ROI in every case.

Optionally, the travel time interval I to be analyzed, and thus the ROI, can be additionally enlarged by a defined "allowance" (e.g. ±5%, ±10%, ±15%) added to the maximum or minimum sound velocity to be presumed. This constitutes an advantageous development of the above-mentioned embodiment. It can thus be accomplished that a near-surface region with a defined, in particular constant, thickness of, for example 30 to 60 mm, preferably 40 mm and above, is always being examined.

According to the development of the method according to an embodiment of the invention, the analysis with regard to flaw signals Fi of the ultrasonic echo signal recorded from the workpiece at the angle Theta is limited to the selected travel time interval I which corresponds to the (e.g. near-surface) region of the workpiece to be inspected.

In its development, an embodiment of the invention provides a practical method for an effective data reduction to an ROI to be individually defined by the user for the respective inspection task. This effective data reduction permits the use of very high pulse repetition rates in the range of up to a few kHz and a highest temporal resolution in the analysis of the ultrasonic echo signals. Moreover, near-surface flaws in the workpiece can be reliably detected by means of the method and the device, even in the case of a ragged workpiece geometry and further components possibly mounted on the workpiece surface, wherein the method and the device can be applied so effectively that excessively long inspection times are avoided.

In an alternative approach, which is also to be comprised by an embodiment of the invention, the echo signal recorded in a time-resolved manner is digitized substantially over a travel time interval I from the entry into the workpiece to the double travel time until the first incidence upon the internal workpiece surface on the side opposite from the test probe, whereby a comprehensive raw data set is generated. This is reduced to a subset of data points to be analyzed by selecting only those data points whose origins lie in the previously defined ROI. With regard to their result, both approaches lead to the selection of the same subset of data points/echo signals to be analyzed. With regard to their results, they are therefore to be considered as equivalent.

A device according to an embodiment of the invention is provided for a non-destructive inspection of a rotationally symmetric workpiece with a diameter that changes from section to section by means of a non-destructive inspection method, e.g. by means of ultrasound in accordance with the pulse echo method. In particular, it is suitable for inspecting forged solid shafts of wheel sets of rail vehicles. A device according to an embodiment of the invention comprises at least one control unit configured to:

generate by means of the inspection technique a test data set characterizing the material properties of the workpiece, with the test data being respectively assigned to a defined test volume Vi in the workpiece, whose position in the workpiece is defined by an azimuth angle $Beta_i$, a radial distance Ri from the axis of symmetry S of the workpiece, and an X position Xi relative to the axis of symmetry S of the workpiece, the test data set including a partial set T of test data from a plurality of test volumes Vi having a common X position Xi and a common radial distance R but different azimuth angles $Beta_i$, form an azimuth angle-dependent indicated value set Ai from the partial set T, wherein this formation includes the differentiation of the partial set T with respect to the azimuth angle Beta, and generate a representation of the workpiece, wherein the elements of the indicated value set Ai are depicted in the representation in a spatially resolved manner.

In an embodiment, the control unit of the testing device is furthermore configured to carry out a threshold analysis for the amplitude of the local slope values that result during the differentiation of the partial set T with respect to the azimuth angle Beta. In particular, the control unit, in an embodiment of the invention, is further configured to set elements of the indicated value set to zero depending on the threshold analysis.

In particular, a device according to an embodiment of the invention is suitable for carrying out the method according to an embodiment of the invention. In some developments of the device, the above-described embodiments of the method are implemented in the control unit. Therefore, these different embodiments in particular permit the realization of those advantages that were already discussed in connection with the method according to embodiments of the invention, to which reference is made here.

In another development, the testing device comprises a guiding device configured to orient the test probe relative to the axis of symmetry S of the workpiece in such a way that the sound path W of the ultrasonic test pulse in the workpiece and the axis of symmetry S span a common plane, the insonification plane P. This means that the travel direction of the ultrasonic test pulses insonified by the test probe into the workpiece has one component in the direction of the axis of symmetry of the workpiece. By ensuring the above-described travel direction of the ultrasonic test pulses insonified into the workpiece using the guiding device, a particularly simple sound field results in the workpiece. This simplifies the subsequent signal processing and evaluation.

In a development of the testing device according to an embodiment of the invention, the test probe comprises an ultrasonic transducer divided into a plurality of individually controllable transducer segments. Such test probes are known from the prior art; they are referred to as "phased array" test probes and, for example, permit the electronic control of the insonification angle of the ultrasonic pulses generated by the ultrasonic test probe into the workpiece, given a suitable electronic control of the individual transducer segments. Ultrasonic test probes according to the teaching of the family of PCT/EP2010/056614 are used with particular preference. In an embodiment, the control unit is furthermore configured to control a test probe of the phased array type in the aforementioned manner so that the insonification angle Theta into the workpiece can be set electronically. Moreover, the control unit is configured to insonify by means of the test probe a series of ultrasonic test pulses into the workpiece at different insonification angles Theta.

In another development of the testing device according to an embodiment of the invention, the latter moreover comprises a rotating device. The rotating device is configured to generate a relative movement of the test probe and the workpiece, in such a way that the workpiece is rotated about its axis of symmetry S under the test probe. In an embodiment, the rotating device comprises a means for acquiring the rotation angle Delta of the relative movement, e.g. an encoder. Moreover, in an embodiment, it is connected to the control unit of the testing device in such a way that the acquired rotation angle Delta of the rotary movement can be transmitted to the control unit. In a simplified embodiment of this device, it is not the angle of the relative movement of the test probe and the workpiece that is actually applied by the rotating device which is acquired and transmitted by the rotating device to the control unit. Rather, the control unit is configured for controlling the rotating device in such a way that the latter generates a relative movement of the test probe and the workpiece about a rotation angle Delta predetermined by the control unit. An acquisition of the angle of the rotary movement that is actually executed does not have to be carried out in this case, i.e. an encoder, for example, can be omitted.

In another development of the testing device according to an embodiment of the invention, the test probe of the testing device comprises two ultrasonic transducers. They are characterized in that the travel direction of a first part of the pulses has one component in the direction of the axis of symmetry S of the workpiece and the travel direction of a second part of the pulses has one component oriented contrary to the direction of the axis of symmetry S. A particularly compact construction is provided if the two ultrasonic transducers are mounted on a common leading body, which may, for example, consist of polystyrene, polycarbonate or Plexiglas and can be disposed in a common test probe housing.

Finally, the device according to an embodiment of the invention comprises a display unit, e.g. an LCD, connected to the control unit. The control unit is in that case configured to generate a graphic representation of the workpiece on the display unit.

BRIEF DESCRIPTION OF THE DRAWINGS

Other advantages and features are apparent from the dependent claims as well as from the following exemplary embodiments. The exemplary embodiments are to be understood not to be limiting; they serve for rendering the invention described above in a general manner comprehensible to the person skilled in the art. The exemplary embodiments will be explained with reference to the drawing. In the drawing:

FIG. 6: shows a C image recorded on the solid shaft section according to FIG. 3, and FIG. 7: shows a three-dimensional representation of the solid shaft section from FIG. 3 with detected flaws signals Fi drawn in.

DETAILED DESCRIPTION

Figure 1:
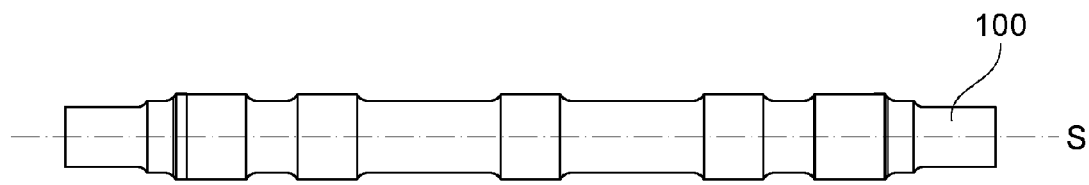
FIG. 1: shows a side view of a typical solid shaft of a wheel set of a rail vehicle.

FIG. 1 shows a side view of a typical solid shaft 1 of a wheel set of a rail vehicle. It is a rotationally symmetric forging with a diameter changing from section to section, as becomes clear from FIG. 1. In particular, the shaft 1 comprises different sections with a constant diameter, which are provided for accommodating the wheel hubs, the rolling bearings, with which the solid shaft is rotatably mounted on the rail vehicle, and a centrally disposed brake disk. As a forging, a solid shaft according to FIG. 1 typically has a certain anisotropy of the sound velocity for ultrasound, which is produced by local structural changes caused by the forging process. In this case, the solid shaft 1 is rotationally symmetric to the drawn-in axis of rotation S.

Figure 2:
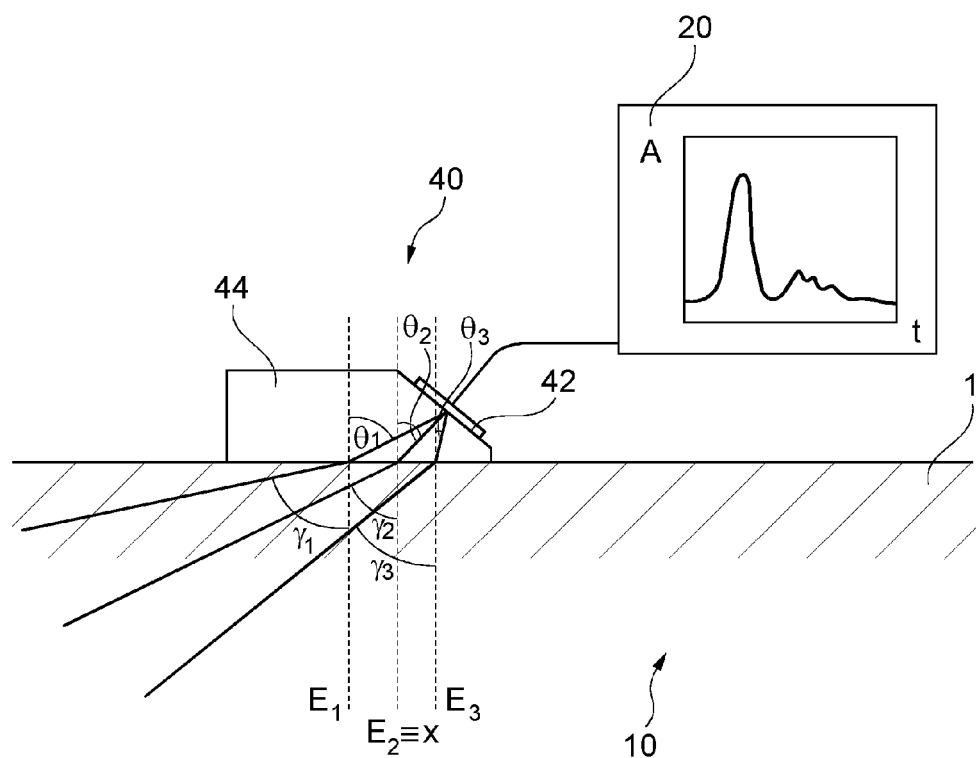
FIG. 2: shows a schematic representation of a test probe and a control unit according to a first exemplary embodiment of a testing device.

FIG. 2 shows a first exemplary embodiment of a testing device 10, which comprises a control unit 20 and a test probe 40 connected to it. The test probe 40 comprises a segmented ultrasonic transducer 42 of the phased array type. It therefore comprises a plurality of individually controllable transducer elements (not shown). In this case, the segmented ultrasonic transducer 42 is disposed on a leading body 44 which in turn consists of a material suitable for oblique insonification into a forged steel workpiece. The leading body 44 often consists of polystyrene, polycarbonate or Plexiglas®. Generally, both the leading body 44 as well as the segmented transducer 42 are disposed in a common test probe housing (not shown) in order to shield them from environmental influences. In FIG. 2, the test probe 40 is shown placed on the cylindrical surface of a rotationally symmetric workpiece 1, which can be, for example, the solid shaft 100 shown in FIG. 1. The contact surface which is formed by the leading body 44 and with which the test probe is placed on the surface of the workpiece 1 therefore also has a hollow-cylindrical shape whose internal diameter is matched to the external diameter of the workpiece 1. As was already explained in the introduction, there are a lot of different shaft geometries that can also be completely curved in the longitudinal direction, i.e. it is possible that the workpiece to be inspected has no purely cylindrical region with a constant diameter. Using the technical teaching known from PCT/EP2010/056614, the use of test probes whose leading bodies are adapted to the cross section of the workpiece both in the longitudinal direction as well as the transverse direction is also possible. This adaptation is generally effected locally, i.e. for a predetermined X position relative to the axis of symmetry S of the workpiece.

The control unit 20 is configured for controlling the test probe 40 in such a way that it generates an ultrasonic test pulse that is coupled into the workpiece 1 at a defined insonification angle Theta. Furthermore, the control unit 20 is configured to adjust the insonification angle Theta in a controlled manner. By way of example, FIG. 2 shows three sound paths of three ultrasonic test pulses coupled into the workpiece 1 at different insonification angles Theta 1, Theta 2 and Theta 3. While the insonification angles Theta 1, Theta 2 and Theta 3 can be controlled with very good accuracy by the control unit 20, the entrance angles Gamma 1, Gamma 2 and Gamma 3 resulting in the workpiece 1 are associated with a certain uncertainty that is directly linked to the above-mentioned anisotropy of the sound velocity for ultrasound in the forged solid shaft 100. It is also immediately apparent from FIG. 2 that, given a constant test probe position X, the coupling location E changes slightly if the insonification angle Theta is varied, due to the refraction during the transition into the workpiece, i.e. given a constant position X, a different coupling location E1,2,3 is obtained for each insonification angle Theta1,2,3. If the requirements with respect to the accuracy of the inspection are not too high, this effect can be neglected, e.g. in determining the position w at which the sound path W hits the internal workpiece surface for a given insonification angle Theta and a given test probe position X. In the case of higher requirements with regard to accuracy, it can be taken into account by calculation, e.g. when determining the position w.

Furthermore, the control unit 20 is configured to record, by means of the test probe 40, an ultrasonic echo signal in a time-resolved manner from the workpiece 1, at the angle Theta, and to then digitize it in a selected travel time interval I. In this connection, the control unit 20 is configured to select a travel time interval I depending on the sound path W of the ultrasonic test pulse in the workpiece 1, with this selected travel time interval corresponding to a near-surface region of the workpiece 1. As was already mentioned in the introduction, the sound path of the ultrasonic test pulse in the workpiece is generally dependent on the workpiece geometry, the test probe position X as well as on the insonification angle Theta and the inclination angle Phi and on the acoustic properties of the workpiece. In particular, the control unit 20 can be configured to permit the user to autonomously define the above-mentioned near-surface region depending on the workpiece geometry. In this case, the specifically selected test probe position can also be taken into account.

In an embodiment, the ROI is defined via the travel time interval I selected (and thus to be analyzed) for a given insonification angle Theta. The basis is the sound velocity for the ultrasonic test pulse in the workpiece, which can be specified only with a certain uncertainty. The start of the travel time interval I is defined by the time $2tROI\_EIN$ at which the ultrasonic test pulse hits the internal surface for the first time at the earliest, i.e. the highest possible sound velocity is generally used as a basis. The end of the travel time interval I is defined by the time $2tROI\_AUS$ at which the ultrasonic test pulse hits the internal surface for the first time at the latest, i.e. the lowest possible sound velocity is generally used as a basis. In individual cases, deviations may result due to the workpiece geometry and the change of travel paths W due to the change of the entrance angle Gamma (cf. FIG. 2) in the case of a variation of the sound velocity. It is thus ensured that the ultrasonic test pulse hits the internal workpiece surface in the selected travel time interval I with certainty, i.e. the internal surface lies within the ROI in every case.

Optionally, the travel time interval I to be analyzed, and thus the ROI, can be additionally enlarged by a defined "allowance" (e.g. ±5%, ±10%, ±15%) added to the maximum or minimum sound velocity to be presumed. This constitutes an advantageous development of the above-mentioned embodiment. It can thus be accomplished that a near-surface region with a defined, in particular constant, thickness of, for example, 30 to 60 mm, or 40 mm and above, is always being examined.

As mentioned above, the control unit 20 is configured to select a "near-surface" travel time interval I. Then, the control unit 20 digitizes and analyzes the recorded ultrasonic echo signals in the selected "near-surface" travel time interval I with regard to flaw signals Fi, i.e. with regard to ultrasonic echo signals that indicate near-surface flaws in the workpiece 1, such as incipient cracks or near-surface defects. In the simplest case, only a maximum echo amplitude in the travel time interval I is determined here, and no assessment of the echo amplitude as a "flaw signal Fi" or "no flaw signal" is made. Rather, the echo amplitude (or a similar value obtained in a more discriminate manner) itself is considered as a flaw signal Fi, i.e. there is at least one flaw value Fi for each test probe position X, each insonification angle Theta and each rotation angle Delta (see below).

Figure 3:
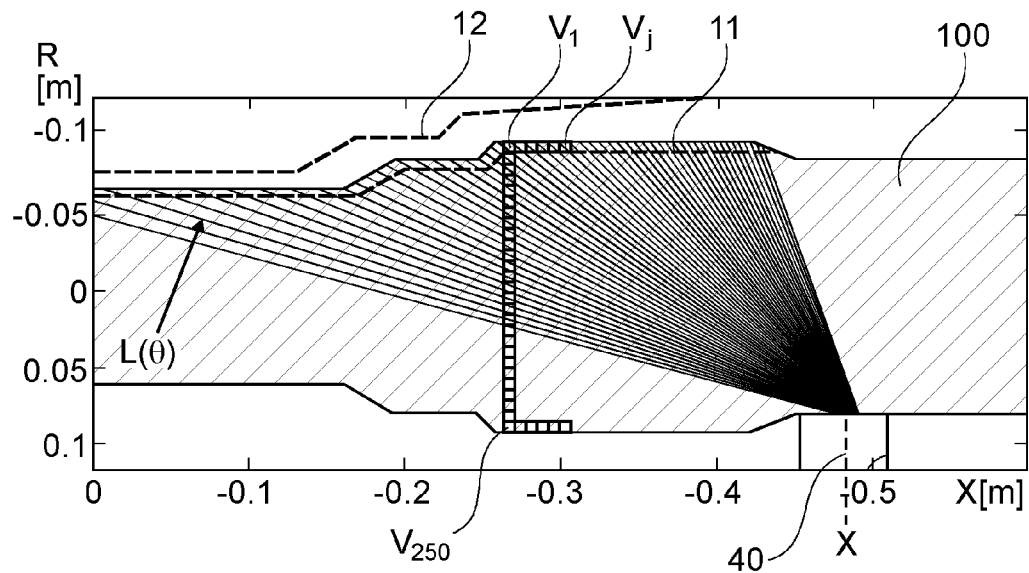
FIG. 3: shows a partial sectional representation through the solid shaft from FIG. 1 for illustrating the sound paths of the ultrasonic test pulses in the workpiece and the ROI.

The concept according to an embodiment of the invention of the selection of a near-surface region, the region of interest, is illustrated by means of FIG. 3, which presents a partial sectional representation of the solid shaft 100 from FIG. 1. FIG. 3 shows the sound paths W of a plurality of ultrasonic test pulses that are coupled into the workpiece 1 at a substantially constant coupling location E by means of the stationary test probe 40 disposed at the position X on the surface of the workpiece 1. In the process, the insonification angle Theta is successively varied, from one ultrasonic test pulse to the next, between preset limits, which are typically between 20 and 75°. In this way, an extensive section of the internal surface of the solid shaft 100 opposite from the test probe position X or the coupling location E is scanned by the ultrasonic test pulses. For each ultrasonic test pulse insonified into the solid shaft 100 at a certain insonification angle Theta, the test probe 40 acquires in a time-resolved manner the echo signal returning from out of the solid shaft 100 at the angle Theta.

FIG. 3 furthermore indicates schematically that the ROI is divided into a plurality of test volumes Vi whose thickness in the radial direction just about corresponds to the local thickness of the ROI. The length of the volumes Vi in the X direction is determined by the pitch $\Delta$Theta of the tuning of the insonification angle Theta. The position of the respective test volumes Vi is determined by a point wi on the surface of the workpiece 1, which in the present example is given by the location of the first incidence of the ultrasonic test pulse on the inner surface of the workpiece 1. In this case, the uncertainty with regard to the entrance angel Gamma resulting from the uncertainty with respect to the local sound velocity, and the uncertainty with regard to the location of the first incidence on the internal surface of the workpiece 1 resulting therefrom, is neglected in an embodiment. Within the context of the exemplary embodiment, exactly one test volume Vi is assigned to the sound path W that results from the coupling location E at the insonification angle Theta, namely the test volume disposed at the location of the first incidence on the internal surface of the workpiece 1 of the ultrasonic test pulse propagating along the sound path W. In the circumferential direction, the thickness of the test volumes Vi is determined by the pitch $\Delta$Delta with which the workpiece is being rotated about its own axis of symmetry S. In the exemplary embodiment shown, the pitch ΔDelta is 0.72°, so that 500 steps correspond to a complete rotation by 360°. By way of example, FIG. 3 shows a plurality test volumes Vi (i=1, . . . , 250), all of which have the same X and R coordinates (Xi, Ri) and differ only with regard to the azimuth angle Beta.

Figure 7:
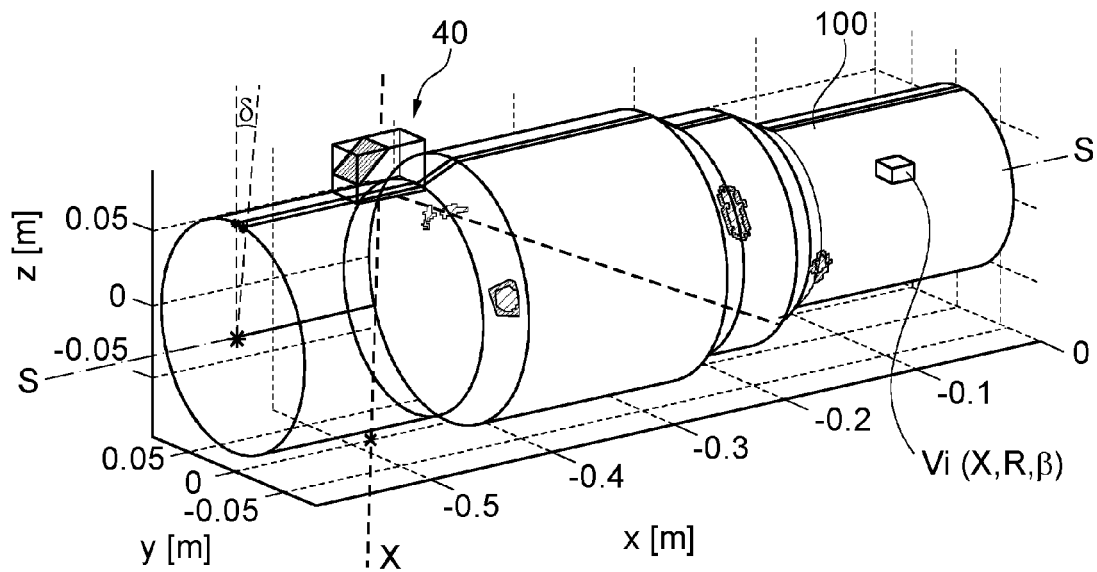

FIG. 7 generally shows a test volume Vi whose position in the workpiece 1 (here: in the solid shaft section 100) is defined by the coordinates X, R and Beta.

If the ROI has been previously defined depending on the geometry of the workpiece 1 to be inspected, as this is indicated in FIG. 3 by the lines 11 and 12, then, given a known coupling location, it is possible for every insonification angle Theta set by the control unit 20 to determine the travel time tROI_EIN until the ultrasonic test pulse insonified into the workpiece 1 at the angle Theta reaches the ROI. Due to the sound velocity in the material of the workpiece 1, which is known per se, this travel time tROI_EIN corresponds to a travel distance $L_{ROI\_EIN}$ in the workpiece, as becomes clear from FIG. 4.

Figure 4:
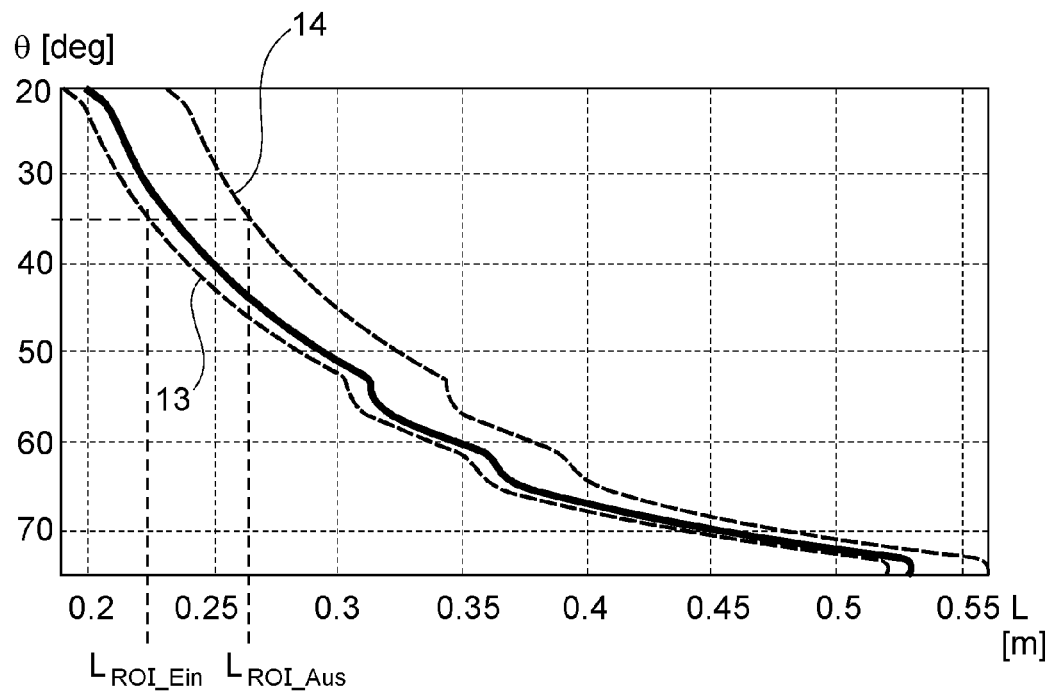
FIG. 4: shows a diagram from which the data reduction due to the introduction of the ROI becomes apparent.

FIG. 4 now shows, for the ROI defined in FIG. 3 by the lines 11 and 12, the value range I of the response time, or the travel distance L, in the solid shaft 100 which has to be analyzed, at a given insonification angle Theta, with regard to relevant flaw signals in order to detect such flaws that are situated in the ROI. By way of example, travel distances $L_{ROI\_EIN}$ (=entrance ROI) as well as $L_{ROI\_AUS}$ (=exit ROI) are drawn in for an insonification angle Theta=350°.

Here, it is possible, at a given test probe position X, for any insonification angle Theta, to record the echo signal in a time-resolved manner for a predetermined duration I after coupling in the ultrasonic test pulse. In this case, the duration I is selected in such a way that, for the selected range of the insonification angle Theta, for the selected test probe position X, as well as for the geometry and the material properties of the workpiece, it is ensured that echo signals from the ROI are always still acquired with regard to time. This means that a digitized echo signal exists for each point within the ROI shown in the diagram according to FIG. 4, which is situated between the lines 13 and 14. According to an embodiment of the invention, only those echo signals from the ROI are examined for flaw signals Fi. Thus, the echo signals to be evaluated are limited by the selection of echo signals that originate from the ROI. Therefore, the lines 11 and 12 from FIG. 3 are in this case translated, based on the physical laws, into the lines 13 and 14 in FIG. 4. The set of those measurement points that lie within these two boundary lines in FIG. 4 then forms a subset of the data points to be analyzed, which is selected according to an embodiment of the invention. This is obtained in accordance with the approach of an embodiment of the present invention by the echo signal, which is provided for a long travel time interval, being digitized and analyzed only within a small window in time I.

Thus, the insight resulting from FIG. 4 is utilized already during the execution of the ultrasound inspection. For a workpiece with known material properties and a known geometry, an ROI is defined analogously to the representation in FIG. 3. For a given test probe position, the relationship between the insonification angle Theta and the response time or travel distance in the workpiece, which is apparent from FIG. 4, is exploited in order to determine, for every insonification angle Theta, the response time interval I in which signals are to be expected that are to be ascribed to flaws in the ROI. For a given test probe position X, the ultrasonic inspection is then limited to the above-mentioned response time interval I for each individual electronically set insonification angle Theta.

Within the context of the method according to an embodiment of the invention, those echo signals that can be traced back to the ROI are subsequently analyzed with respect to flaw indications by the correspondingly configured evaluation unit 20. Within the context of the exemplary embodiment, the echo signals are analyzed for this purpose for every insonification angle Theta and every rotation angle Delta, the analysis being limited to the test volume Vi assigned to the respective sound path by selecting a suitable response time interval I. For example, such a flaw analysis can be based on the amplitude of echo signals, wherein, in this case, use can be made of all of the methods for signal evaluation and, optionally, signal improvement, e.g. for increasing the signal-to-noise ratio, as was already mentioned in the general part.

Within the context of the exemplary embodiment an echo value Gi is determined during the flaw analysis which is assigned to a test volume Vi. This echo value Gi is determined by determining the echo value with the highest amplitude in the travel time interval Ii corresponding to the test volume Vi; the acquired maximum amplitude value Amax constitutes the local echo value G.

The maximum amplitude values Amx registered in the test volumes Vi (i=1, . . . , 250) apparent from FIG. 3 constitute a partial set T of test data according to an embodiment of the invention, which result from test volumes Vi whose X and R coordinates are identical, so that the test data depend only on the rotation angle Delta (or, equivalently, on the azimuth angle Beta). By differentiating (or finding a derivative of) this partial set T with respect to the azimuth angle Beta, signals are being generated according to an embodiment of the invention which accompany the change of the test data in the case of a change of the azimuth angle Beta, which can be obtained, for example, by means of a rotation of the workpiece about its axis of symmetry S by an angle of rotation Delta.

Figure 5:
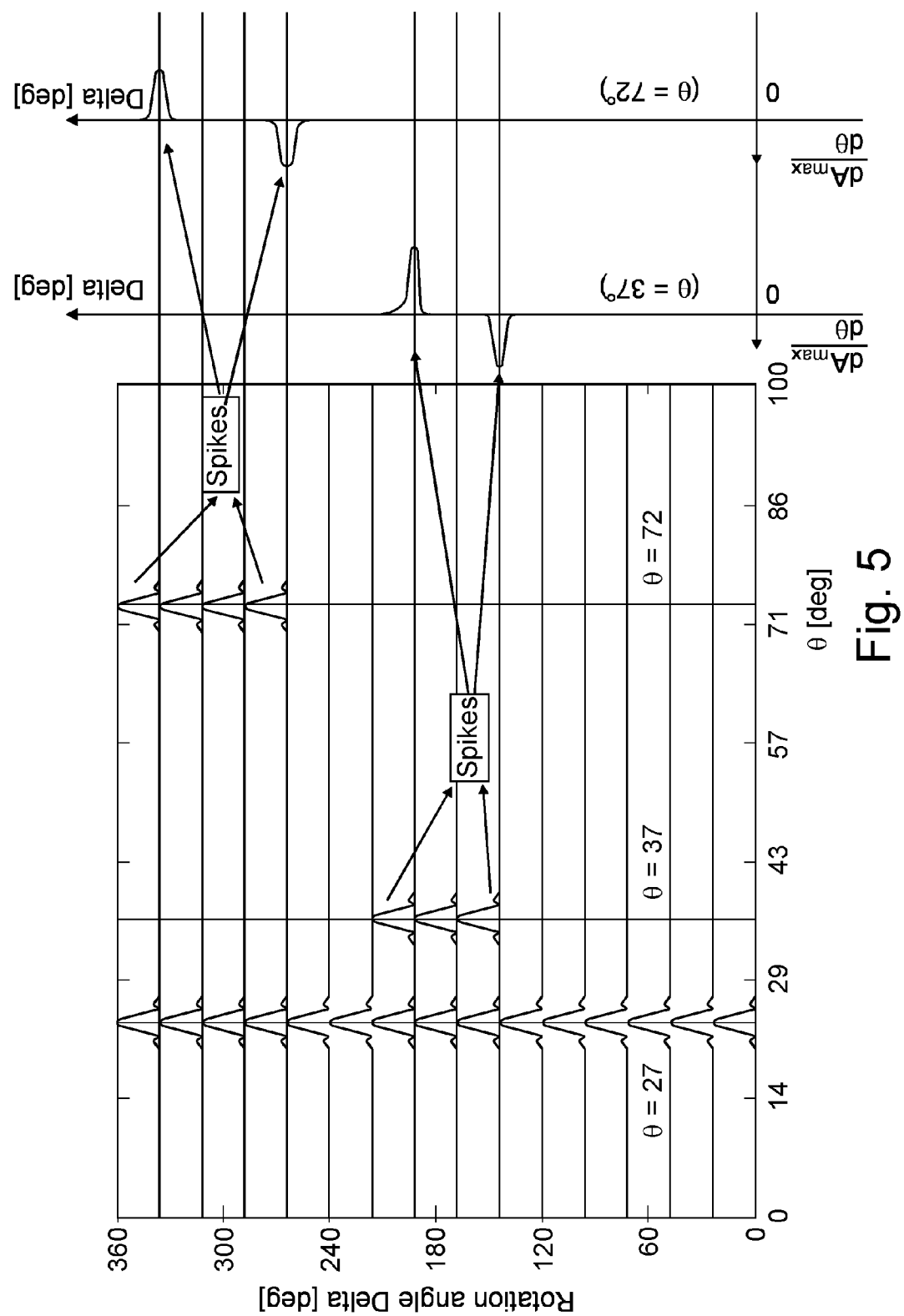
FIG. 5: shows a diagram from which the maximum echo amplitudes Amax, which result from a scan of the angle Theta at a constant rotation angle Delta and fixed insonification location E in the associated test volume, become apparent.

Test data according to a partial set T that are correlated with rotationally symmetric geometric structures and are thus to be assigned to test volumes Vi with the same coordinates Ri and Xi are identical within the limits of measuring accuracy. Such structures always generate the same echo signal irrespective of the angle of rotation Delta, for example in the case of an ultrasound inspection by means of an angle test probe placed on the workpiece surface. This is illustrated in FIG. 5, from which the maximum echo amplitudes Amax, which result from a scan of the angle Theta at a constant rotation angle Delta and fixed insonification location E, become apparent, By way of example, it is shown for the insonification angle Theta=27° that the same value Amax for the maximum echo amplitude in the associated test volume results for every rotation angle Delta. This correlates with a change in the diameter of the workpiece 1 which is directly insonified from an insonification location with the X position shown in FIG. 3 at the insonification angle Theta=27° and thus produces a strong geometry echo (which is independent of the rotation angle).

Within the limits of measuring accuracy as well as the artifacts that typically occur during numerical differentiation of a series of discrete values, the result of the differentiation of this partial set T (which is determined by the insonification angle Theta=27° and the X position of the coupling location E and to which fixed coordinates in the X and R directions can be assigned) with respect to the azimuth angle, irrespective of the azimuth angle, is therefore the value zero.

This situation changes if there is a rotation angle-dependent local inhomogeneity (or, equivalently, a local inhomogeneity that is dependent on the azimuth angle Beta). In that case, a clearly visible echo signal, which is generally limited to a few discrete rotation angle values, occurs, which in turn becomes visible in FIG. 5 due to increased maximum amplitude values Amax assigned to the associated test volumes Vi. By way of example, FIG. 5 shows two local inhomogeneities that, at the insonification angle Theta=37° and Theta=72°, cause significantly increased amplitude values Amax at some rotation angles Delta.

This echo signal ("flaw echo"), which as a rule is limited to a few discrete rotation angle values Delta, causes the occurrence of at least two signals in the derivative formed by differentiation. Thus, the rising signal edge, which is produced during the gradual increase of the rotation angle, generates a "spike" (a sharp local amplitude maximum in the derivative) with a positive maximum. In contrast, the falling signal edge, which results during the further increase, generates a negative spike. The derivative has a zero-crossing point between these edges of the flaw echo. In this example, the local slope values formed by differentiation are close to zero between the spikes. The spikes correlated with the insonification angle Theta=32° and Theta=72° are also shown in the diagram at the edge of FIG. 5, which shows, by way of example, the profile of the derivative of the maximum amplitude Amax as a function of the rotation angle Delta for these two insonification angles Theta.

An embodiment of the invention is now based upon carrying out a signal processing based on the results of the differentiation, in order to generate a graphic representation of the result of the inspection method.

In the exemplary embodiment shown, the elements of the indicated value set Ai also consist of the coordinates (Xi, Ri, Beta$_i$) of the respective test volume Vi and the assigned maximum echo amplitude Amax. In order to produce the representation 50, however, all of those echo amplitudes that are not assigned to a test volume Vi are set to zero, in which the value formed by differentiation for the test volume Vi exceeds the preset threshold, or which lies between a test volume Vi in which the preset positive threshold is exceeded and a test volume Vi in which the preset negative threshold is exceeded.

For the flaw echo detected at the insonification angle Theta=32°, this would be the three maximum echo amplitudes Amax (Theta=32°) apparent from FIG. 5 for the rotation angles Delta1,2,3=144°, 168° and 192°, for the insonification angle Theta=72°, this would be the four maximum echo amplitudes Amax (Theta=72°) apparent from FIG. 5 for the rotation angles Delta1,2,3=264°, 288°, 312° and 336°. All other elements of the indicated value set are set to zero.

Figure 6:
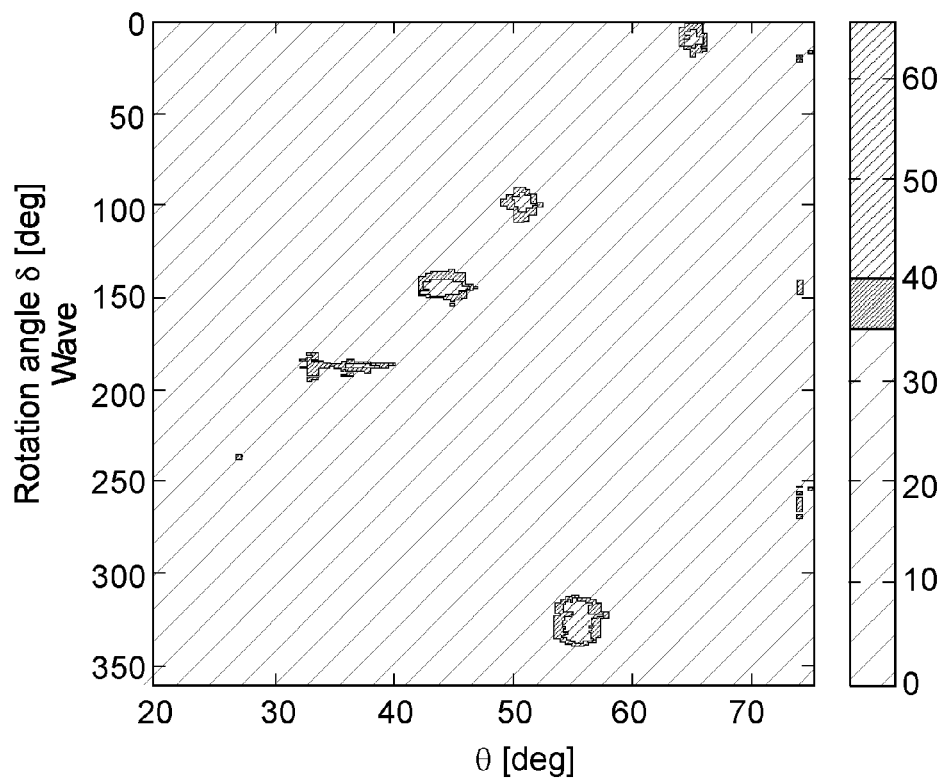

FIG. 7 illustrates the actual conditions in an inspection task on a rotationally symmetric workpiece 1. In this case, FIG. 6 is a three-dimensional representation 50 generated according to an embodiment of the invention of the shaft section of the solid shaft 100 from FIG. 1 apparent from FIG. 3. A guiding device (not shown) is provided with which the test probe 40 is retained on the surface of the solid shaft 100 while maintaining the position X (X position in FIG. 7) relative to the axis of symmetry S and the orientation of the test probe 40 (characterized by the inclination angle Phi relative to the insonification plane P). In the exemplary embodiment shown the inclination angle Phi is 0°.

While the inspection method is carried out, the solid shaft 100 is rotated, by means of a rotating device which is not shown, by 360° or an integral multiple thereof about its axis of symmetry S, which coincides in FIG. 7 with the X axis. The rotation angle of the solid shaft about its axis of symmetry is in this case referred to as Delta; it is acquired by means of a suitable angle encoder (not shown). At a fixed X position of the test probe 40, the entire range of the insonification angle Theta accessible by means of the test probe 40 is electronically tuned for every rotation angle Delta by means of the control unit 20. For each individual insonification angle Theta, the echo signal is recorded in a time-resolved manner and digitized in the selected travel time interval I (Theta). The data points thus obtained can be plotted in a diagram according to FIG. 4. That is, from the entirety of the recorded echo signals, those are being selected, with regard to time, that correspond to the selected ROI. These echo signals are then digitized, i.e. a set of data points to be analyzed are generated for a given insonification angle Theta.

To each individual point w on the surface of the solid shaft 100, an echo value G(w) is assigned which corresponds to the maximum echo amplitude Amax from the test volume assigned to this point. If this method is carried out for a plurality of rotation angles Delta, which can, for example, be gone through gradually in steps of ΔDelta equal to 0.5° or 1° up to a total rotation angle Delta of at least 360°, then it is possible to plot the echo values obtained into a so-called C image. In such a C image, the echo values G assigned to the test volumes Vi are plotted into a diagram according to FIG. 6, in which, for example, the insonification angle Theta is used as the abscissa and the rotation angle Delta of the solid shaft 100 as the ordinate. In this case, the local echo value G(w) can be coded, for example, by means of brightness values or in color. A three-stage scale was used in FIG. 6. If an echo value G remains below a registration limit, then this point is marked brightly in the C image according to FIG. 6. If it exceeds a registration limit but does not yet have to be assigned to a flaw size that is considered critical, then it is coded with a second (e.g. darker, e.g. orange) color value. Finally, if the echo value G exceeds a value that is assigned to a critical flaw size, it is coded with a third color value, e.g. in the signal color red. The additionally applied threshold analysis, which was already mentioned, in this case leads to a significant signal improvement, because rotation angle-independent signals, which very probably are caused by geometric structures of the workpiece 1, are suppressed in this way.

The diagram according to FIG. 6, which results in this way, already has a high informative value for an expert user of a device according to an embodiment of the invention.

The interpretability of the result according to FIG. 7 is improved yet again if it is not the insonification angle Theta that is used as the abscissa, but the X position (position relative to the axis of symmetry S of the workpiece) of the point w on the workpiece surface assigned to the associated test volume Vi. The representation that results in this manner substantially corresponds to the representation according to FIG. 6, but is suitable for a direct transfer onto the three-dimensional representation of the examined solid shaft 100 of FIG. 7 generated according to an embodiment of the invention. The color-coded signal values are then plotted on the surface of the three-dimensionally represented workpiece depending on the rotation angle Delta of the shaft 100 and on the position on the axis of symmetry of the shaft 100 (position on the X axis). The result is the flaw representation apparent from FIG. 7, which has an enormously improved interpretability over the visualization methods known so far from the prior art.

Particular advantages also result, in particular, when the representation according to FIG. 7 is designed in such a way that a rotation of the shaft 100 about its axis of symmetry S can be shown. This is possible, for example, in a CAD model of the solid shaft 100 with the echo values G(w) plotted in a spatially resolved manner on its surface. A moving representation of the rotation of the solid shaft 100 about the rotation angle Delta as a sequence of individual images that combine into a film is also conceivable, and protection is sought therefor.

The invention claimed is:

1. A method for non-destructive inspection of a rotationally symmetric workpiece having sections with different diameters, the method comprising:
generating a test data set characterizing material properties of the workpiece, wherein elements of the test data set are respectively assigned to a defined test volume Vi in the workpiece, the test volume Vi being a division of a region of interest that is defined based on a selected travel time interval, a position of the test volume Vi in the workpiece being defined by an azimuth angle, a radial distance from an axis of symmetry of the workpiece, and an X position relative to the axis of symmetry of the workpiece, the test data set comprising a partial set of several elements assigned to a plurality of test volumes having a common X position and a common radial distance and different azimuth angles;
forming an azimuth angle-dependent indicated value set, wherein this forming comprises differentiation of the partial set with respect to the azimuth angle; and
generating a representation of the workpiece, wherein elements of the indicated value set are depicted in the representation in a spatially resolved manner.

2. The method according to claim 1, wherein a threshold analysis is carried out in the forming step for the amplitude of the local slope values that result during the differentiation of the partial set with respect to the azimuth angle.

3. The method according to claim 1, wherein the indicated value set is a subset of the test data set.

4. The method according to claim 2, wherein, depending on the threshold analysis, elements of the indicated value set are set to zero.

5. The method according to claim 1, wherein the test data are obtained by insonifying ultrasonic test pulses into the workpiece at different coupling locations at different defined insonification angles and subsequent recording of the ultrasonic echo signals resulting from one insonified ultrasonic test pulse, respectively, from the workpiece at the coupling location at the insonification angle.

6. The method according to claim 5, wherein a coupling location is characterized by an azimuth angle, a radial distance Rei from the axis of symmetry of the workpiece, and an X position relative to the axis of symmetry of the workpiece, and that a plurality of test data is obtained by insonification at a fixed insonification angle, starting at coupling locations whose radial distances and X positions are identical but which differ with regard to the azimuth angle.

7. The method according to claim 6, wherein the azimuth angles of the coupling locations cover the interval [0°, 360°].

8. The method according to claim 1, wherein the representation presents the surface of the workpiece two-dimensionally or three-dimensionally.

9. The method according to claim 5, wherein a point on the surface of the representation of the workpiece, at which the associated element of the indicated value set depicted, is assigned to the sound path of an ultrasonic test pulse insonified into the workpiece at the coupling location at the defined insonification angle in the workpiece.

10. The method according to claim 1, wherein the elements of the test data set are respectively obtained by analysis of the recorded ultrasonic echo signals in the travel time interval, the travel time interval being selected dependent on the associated sound path in the workpiece.

11. The method according to claim 10, wherein the elements of the test data set are formed by the largest amplitudes of the ultrasonic echo signal occurring in the respectively selected travel time interval.

12. The method according to claim 10, wherein the selected travel time interval corresponds to a near-surface region of the workpiece.

13. The method according to claim 10, wherein the travel time interval is selected in such a way that the respective ultrasonic test pulse reaches the surface of the workpiece within the travel time interval.

14. The method according to claim 5, wherein insonification for each ultrasonic test pulse takes place in such a way that its sound path in the workpiece and the axis of symmetry of the rotationally symmetric workpiece span a common plane.

15. A testing device for non-destructive inspection of a rotationally symmetric workpiece having sections with different diameters, the testing device comprising:
a control unit configured to:
generate a test data set characterizing material properties of the workpiece, wherein elements of the test data are respectively assigned to a defined test volume in the workpiece, the test volume Vi being a division of a region of interest that is defined based on a selected travel time interval, a position of the test volume Vi in the workpiece being defined by an azimuth angle, a radial distance from the axis of symmetry of the workpiece, and an X position relative to an axis of symmetry of the workpiece, the test data set comprising a partial set of test data from a plurality of test volumes having a common X position and a common radial distance and different azimuth angles,
form an azimuth angle-dependent indicated value set from the partial set, wherein this forming comprises differentiation of the partial set with respect to the azimuth angle, and
generate a representation of the workpiece, wherein elements of the indicated value set are depicted in the representation in a spatially resolved manner.

16. The testing device according to claim 15, wherein the control unit is further configured to carry out a threshold analysis for the amplitude of the local slope values that result during the differentiation of the partial set with respect to the azimuth angle.

17. The testing device 10 according to claim 16, characterized in that wherein the control unit is further configured to set elements of the indicated value set to zero depending on the threshold analysis.

18. The testing device according to claim 15, further comprising:
a test probe for insonifying an ultrasonic test pulse into the workpiece at a defined insonification angle and for recording an ultrasonic echo signal from the workpiece, wherein the control unit is further configured to:
control the test probe for insonifying an ultrasonic test pulse into the workpiece at a defined insonification angle,
record an ultrasonic echo signal at the defined insonification angle from the workpiece,
select the travel time interval depending on a sound path of the ultrasonic test pulse in the workpiece, and
iv) generate, by analyzing the recorded ultrasonic echo signal in the selected travel time interval, an echo value forming an element of the test data set.

19. The testing device according to claim 18, wherein the selected travel time interval corresponds to a near-surface region ROI of the workpiece.

20. The testing device according to claim 19, wherein the ultrasonic test pulse reaches the surface of the workpiece within the selected travel time interval.

21. The testing according to claim 18, further comprising a guiding device configured to orient the test probe relative to the axis of symmetry of the workpiece in such a way that the sound path of the ultrasonic test pulse in the workpiece and the axis of symmetry of the rotationally symmetric workpiece span a common plane, the insonification plane.

22. The testing device according to claim 18, wherein the test probe comprises an ultrasonic transducer divided into a plurality of individually controllable transducer segments, and the control unit is further configured to insonify a series of ultrasonic test pulses into the workpiece at different insonification angles.

23. The testing device according to claim 18, further comprising a rotating device configured to generate a relative movement of the test probe and the workpiece, in such a way that the workpiece is rotated about its axis of symmetry under the test probe.

24. The method according to claim 14, wherein the test probe comprises a first ultrasonic transducer and a second ultrasonic transducer, and the travel direction of the ultrasonic test pulses insonified by the first ultrasonic transducer into the workpiece, relative to the axis of symmetry of the workpiece, is oriented contrary to the travel direction of the ultrasonic test pulses insonified by the second ultrasonic transducer into the workpiece.

* * * * *